US011051971B2

United States Patent
Schertiger

(10) Patent No.: US 11,051,971 B2
(45) Date of Patent: Jul. 6, 2021

(54) OSTOMY APPLIANCE

(71) Applicant: Coloplast A/S, Humlebaek (DK)

(72) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 532 days.

(21) Appl. No.: 15/769,745

(22) PCT Filed: Oct. 19, 2016

(86) PCT No.: PCT/DK2016/050335
§ 371 (c)(1),
(2) Date: Apr. 20, 2018

(87) PCT Pub. No.: WO2017/067558
PCT Pub. Date: Apr. 27, 2017

(65) Prior Publication Data
US 2018/0311068 A1    Nov. 1, 2018

(30) Foreign Application Priority Data

| Oct. 20, 2015 | (DK) | ............................ PA 2015 70680 |
| Oct. 20, 2015 | (DK) | ............................ PA 2015 70682 |
| May 20, 2016 | (DK) | ............................ PA 2016 70340 |

(51) Int. Cl.
*A61F 5/448* (2006.01)
*A61F 5/443* (2006.01)
*A61F 5/445* (2006.01)

(52) U.S. Cl.
CPC .............. *A61F 5/448* (2013.01); *A61F 5/443* (2013.01); *A61F 5/445* (2013.01)

(58) Field of Classification Search
CPC combination set(s) only.
See application file for complete search history.

(56) References Cited

U.S. PATENT DOCUMENTS

| 4,846,798 | A | * | 7/1989 | Holtermann | ............ A61F 5/448 |
| | | | | | 604/339 |
| 4,923,452 | A | * | 5/1990 | Hunger | .................... A61F 5/448 |
| | | | | | 604/338 |
| 4,929,245 | A | * | 5/1990 | Holtermann | ............ A61F 5/448 |
| | | | | | 604/338 |
| 5,000,748 | A | * | 3/1991 | Fenton | .................... A61F 5/443 |
| | | | | | 604/340 |
| 5,147,340 | A | * | 9/1992 | Lavender | ................ A61F 5/448 |
| | | | | | 604/344 |
| 5,167,651 | A | * | 12/1992 | Leise, Jr. | ................. A61F 5/448 |
| | | | | | 604/339 |

(Continued)

FOREIGN PATENT DOCUMENTS

| BY | 13196 C1 | 6/2010 |
| BY | 13347 C1 | 6/2010 |

(Continued)

*Primary Examiner* — Guy K Townsend
(74) *Attorney, Agent, or Firm* — Coloplast Corp., Coloplast A/S; Nick Baumann

(57) ABSTRACT

An ostomy appliance (20) including a wafer (22) having a first opening (3) configured to be attached to a skin surface (S) around an ostomy (O) of a user, and a bag (34) for collecting stomal output that includes an adhesive flange (42) configured to engage with the peristomal skin surface around the ostomy through the first opening in the wafer.

11 Claims, 6 Drawing Sheets

(56) References Cited

U.S. PATENT DOCUMENTS

| | | | | |
|---|---|---|---|---|
| 5,269,773 A * | 12/1993 | Vidal | .................... | A61F 5/448 604/338 |
| 5,714,225 A * | 2/1998 | Hansen | .................. | A61F 5/443 428/114 |
| 5,785,695 A * | 7/1998 | Sato | ........................ | A61F 5/448 604/338 |
| 5,865,819 A * | 2/1999 | Cisko, Jr. | ................ | A61F 5/445 604/339 |
| 7,722,586 B2 * | 5/2010 | Mullejans | ............... | A61F 5/448 604/342 |
| 8,684,982 B2 * | 4/2014 | Nguyen-DeMary | .... | A61F 5/445 604/337 |
| 2006/0200101 A1 * | 9/2006 | Mullejans | ............... | A61F 5/445 604/339 |
| 2008/0154220 A1 * | 6/2008 | Gaffney | ................. | A61F 5/445 604/333 |
| 2010/0241092 A1 * | 9/2010 | Nguyen-DeMary | .... | A61P 31/00 604/336 |
| 2011/0213321 A1 * | 9/2011 | Fattman | ................. | A61F 5/448 604/344 |
| 2011/0213322 A1 * | 9/2011 | Cramer | ................... | A61F 5/443 604/344 |

FOREIGN PATENT DOCUMENTS

| | | | | |
|---|---|---|---|---|
| EP | 1872751 A2 | | 1/2008 | |
| EP | 2315561 A1 | | 1/2010 | |
| GB | 2290974 A | * | 1/1996 | ............ A61F 5/443 |
| GB | 2290974 A | | 1/1996 | |
| RU | 2118145 C1 | | 8/1998 | |
| RU | 2519961 C2 | | 6/2014 | |
| RU | 2525209 C2 | | 8/2014 | |
| SU | 1605912 A3 | | 11/1990 | |
| SU | 1724004 A3 | | 3/1992 | |
| WO | 03026541 A1 | | 4/2003 | |
| WO | 2009023870 A1 | | 2/2009 | |
| WO | WO-2009023870 A1 | * | 2/2009 | ............ A61F 5/448 |

\* cited by examiner

OSTOMY APPLIANCE

SUMMARY

One aspect of the disclosure provides an ostomy appliance in accordance with the appended claim 1. Another aspect provides a collecting bag for a two-piece ostomy appliance.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
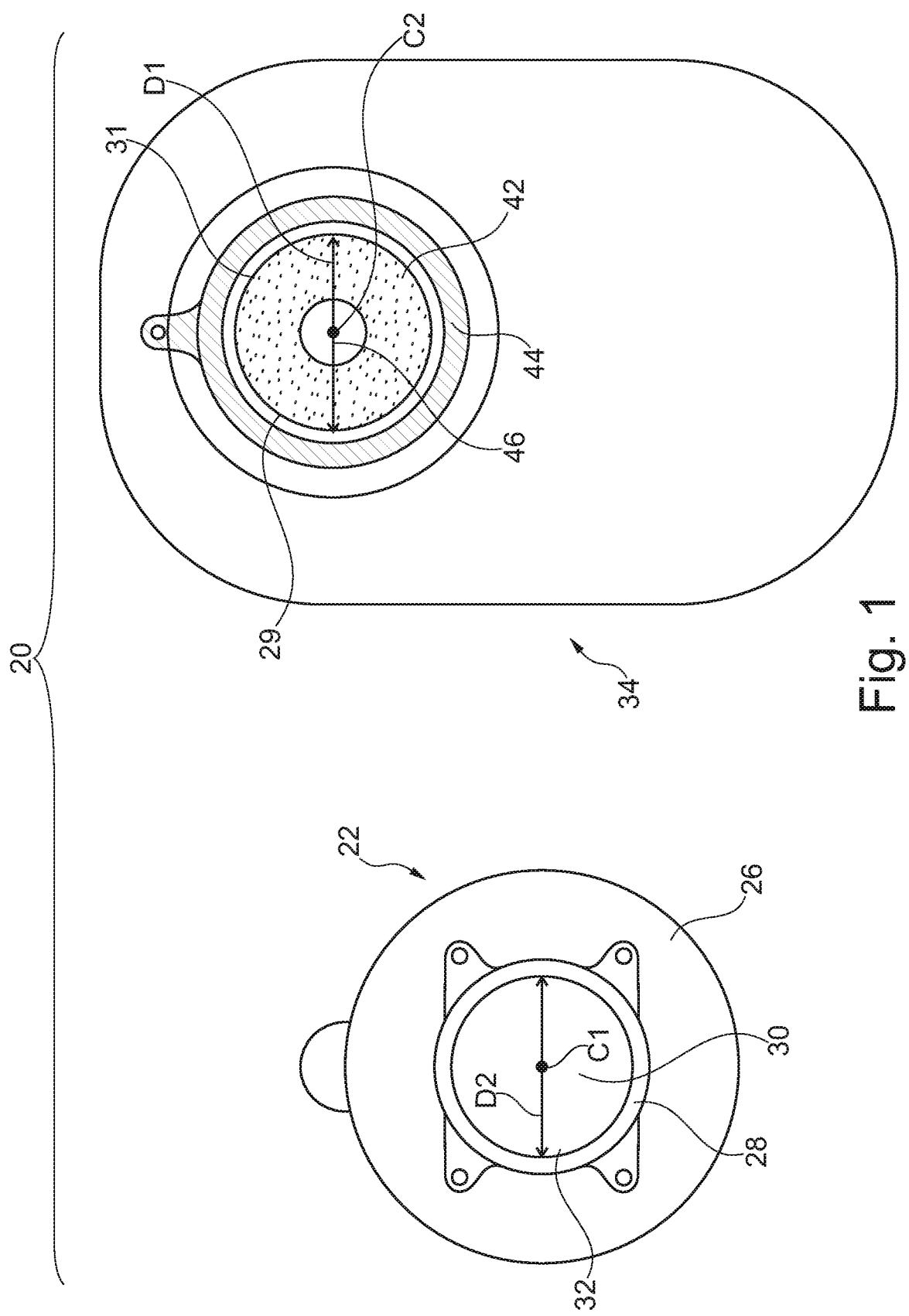
FIG. 1 is a plan view of one embodiment of an ostomy appliance.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following description, whenever referring to proximal side of a device or part of a device, the referral is to the skin-facing side, when the ostomy appliance is worn by a user. When referring to the distal surface or side of a device or element, or parts thereof, the reference is to the surface or side facing away from the skin, at least when the ostomy appliance is in use and worn by a user. Put differently, the proximal surface or side is the side closest to the user, when the appliance is fitted on a user and the distal side is the opposite side—the side furthest away from the user in use.

An axial direction is defined as the direction of the stoma, when the appliance is worn by a user. Thus, the axial direction is substantially perpendicular to a skin surface of a user, such as an abdominal skin surface. A radial direction is defined as transverse to the axial direction.

It is to be understood that the features of the various exemplary embodiments described herein may be combined with each other, unless specifically noted otherwise. Nothing in the description of the different figures shall be taken to mean that a discussed feature is necessarily only applicable to the exact illustration plotted in a related figure, unless obviously recognizable to the opposite effect or specifically noted otherwise.

In the following, the words 'ostomy' and 'stoma' and any related or derived wordings thereof are used interchangeably without any intention to have different meanings.

Embodiments provide an ostomy appliance including a base wafer having a first opening, the base wafer configured to be attached to a skin surface around an ostomy of a user, and a bag for collecting stomal output ('collecting bag') that includes an adhesive flange configured to engage with the peristomal skin surface around the ostomy through the first opening in the base wafer. Embodiments provide an ostomy appliance wherein adhesive material in the peristomal area, i.e. adhesive material that is subject to a majority of aggressive stomal fluids exuding from the ostomy, can be exchanged or substituted with a new adhesive flange each time the collecting bag is exchanged. Embodiments provide an ostomy appliance wherein adhesive material subject to stress from carrying the weight of the stomal output accumulated in the collecting bag is separate from the adhesive material primarily being subjected to the aggressive stomal output fluids. This provides an ostomy appliance that allows for a large degree of differentiation between types of adhesive material because each adhesive can be tailor-made to meet the particular requirements of the location and function of the adhesives. Embodiments provide an ostomy appliance allowing for an increase in wear-time of the wafer, which leads to fewer changes of the adhesive wafer carrying the weight of the bag and thus to less skin irritation caused by attaching and detaching adhesive material from the skin surface.

Embodiments provide a solution wherein the load from the weight of the collecting bag itself and of the accumulated stomal output is carried almost exclusively by adhesive on the proximal side of the base wafer. By 'almost exclusively' is to be understood that any contribution to the load-carrying or load-bearing capability of the ostomy appliance from the adhesive flange is negligible compared to the contribution from the adhesive of the base wafer. In other words, the adhesive on the adhesive flange, which is adapted to be located on the peristomal skin surface of the user, is not required to have load bearing capabilities or characteristics. Instead, the adhesive on the adhesive flange can be optimized towards creating an improved and efficient seal having greater resistance against deterioration caused by stomal output attacking the integrity of the adhesive matrix. This in turn means less skin complications (caused by stomal output) and reduced risk of loss of adhesion (appliance slipping off skin because of breaking-down of adhesive and thus adhesion). Suitable types of adhesives for the adhesive of the adhesive flange include, but are not limited to, paste like adhesives of the types disclosed in WO 2010/069334. In embodiments, more than one type of adhesive material is used for the adhesive of the adhesive flange. In such embodiments, the different adhesive materials can be provided in a side-by-side configuration and/or in a layered configuration on the flange.

Figure 2:
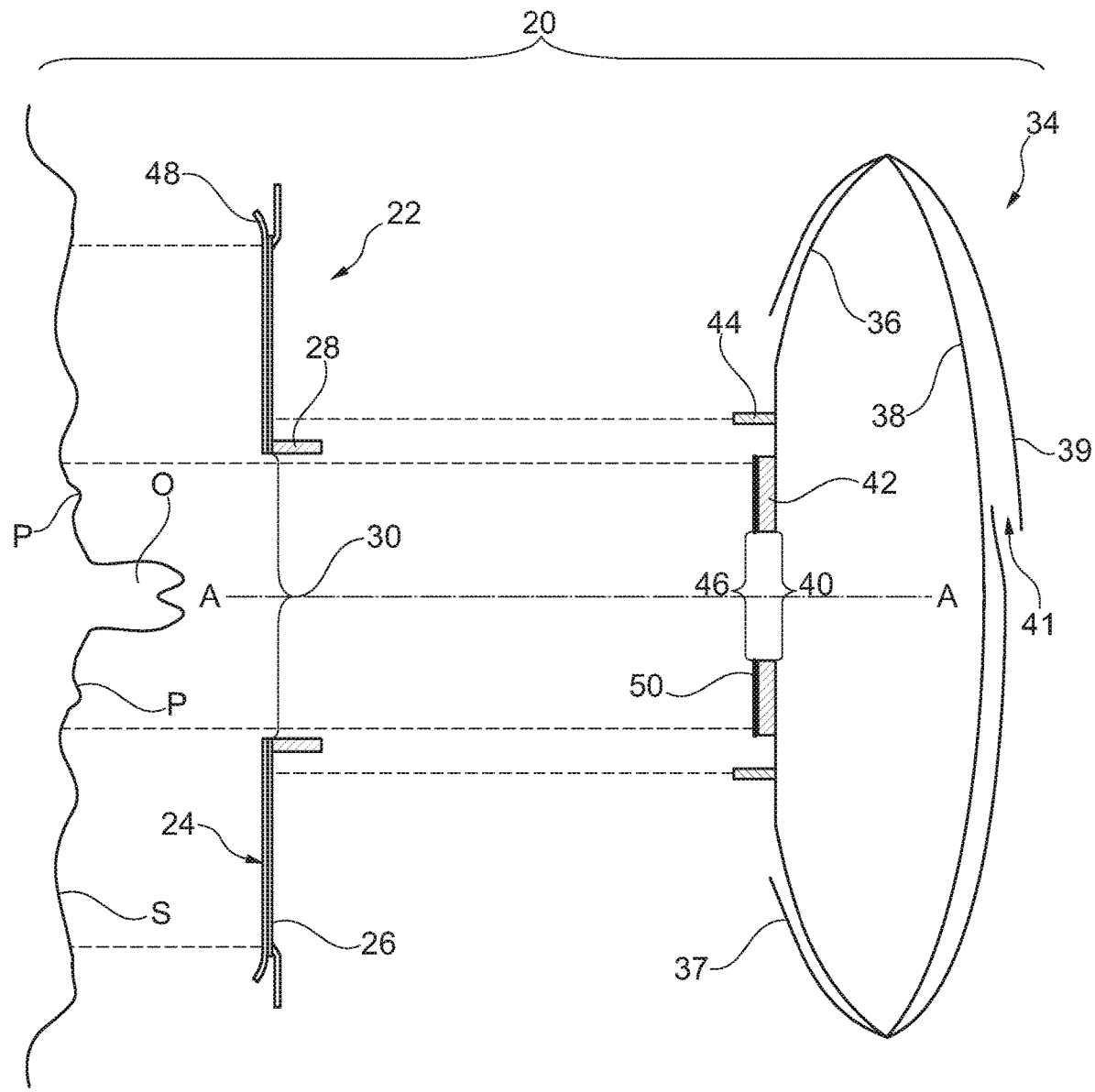
FIG. 2 is a cross-sectional side view of one embodiment of an ostomy appliance.

FIG. 1 is a plan view and FIG. 2 is a cross-sectional side view of an ostomy appliance 20 including a base wafer 22 and a collecting bag 34. The base wafer 22 includes an adhesive proximal side 24 configured to be attached to a skin surface S around an ostomy O of a user (FIG. 2) and a distal side 26. A first half 28 of a coupling is attached to the distal side 26 of the base wafer 22. In embodiments, the first half 28 of the coupling is welded or glued to the distal side 26 of the base wafer 22. In one embodiment, a first opening 30 in the base wafer 22 is defined radially inside of a first inner, peripheral edge 32 of the first half 28 of the coupling.

The collecting bag 34 is adapted to collect stomal output and includes a proximal wall 36 connected to a distal wall 38 (FIG. 2). An inlet hole 40 is located in the proximal wall 36. The inlet hole 40 allows for stomal output exuding out of the stoma O to enter into the collecting bag 34 in use of the ostomy appliance 20.

An adhesive flange 42 is attached to the proximal wall 36 of the collecting bag 34 around the inlet hole 40. In one embodiment, as illustrated by way of example in FIG. 2, a distal surface of the adhesive flange 42 is attached directly (i.e. without any other intermediate layers, sheets or substrates in between) to an external surface of the proximal wall 36 around the inlet hole 40. In one embodiment, the adhesive flange 42 includes adhesive material applied directly onto the external surface of the proximal wall 36 around the inlet hole 40. A second half 44 of the coupling is provided on the proximal wall 36 around the adhesive flange 42. In one embodiment, the second half of the coupling 44 is provided annularly around the adhesive flange 42. The second half 44 of the coupling is attached by welding or adhesion to the proximal wall 36 of the collecting bag 34. In embodiments, the first and second halves 28, 44 of the coupling include, but are not limited to, first and second mechanical coupling halves, first and second engaging flanges where at least one flange has an adhesive provided on it, first and second magnetic coupling parts, first and second hook-and-loop type coupling parts to give some examples. In one embodiment, the first half 28 of the coupling includes a first annular ring and the second half 44 of the coupling includes a second annular ring adapted for frictional engagement with the first annular ring. In another embodiment, the first half 28 of the coupling includes an annular flange and the second half 44 of the coupling includes an annular adhesive ring adapted for adhesive engagement with the annular flange.

The adhesive flange 42 is configured to engage with a peristomal skin surface P around the ostomy O of the user. During use of the ostomy appliance 20, the adhesive flange 42 is adhered to the peristomal skin surface P through the first opening 30 of the base wafer 22. This means that the adhesive flange 42 'reaches through' the first opening 30 in the base wafer 22 in order for the adhesive on the adhesive flange 42 to adhere to the peristomal skin surface P. In other words, the adhesive flange 42 extends or passes axially through (along axis A-A of FIG. 2) the base wafer 22 in the 'open' zone or area defined by the first opening 30 to reach or engage with the peristomal skin surface P.

In embodiments, as illustrated by way of example in FIG. 2, the adhesive flange 42 includes a central opening 46 that is adapted to combine with the inlet hole 40 in the proximal wall 36 of the collecting bag 34 to provide a passage for a user's stoma O, and the adhesive flange 42 is attached directly to the proximal wall 36 around the inlet hole 40. The central opening 46 in the adhesive flange 42 is adapted to locate around the ostomy O to help direct stomal output into the collecting bag 34 through the inlet hole 40. The adhesive of the adhesive flange 42 acts to create a seal to the peristomal skin surface P around the ostomy O such that the stomal output is led through the inlet hole 40 and the central opening 46 to guide the stomal output into the collecting bag 34 rather than entering into contact with the peristomal skin surface P where it is known to cause skin irritation and disintegration of the adhesive. A second half 44 of the coupling is configured to couple to the first half 28 of the coupling to attach the collecting bag 34 to the base wafer 22. Thereby, the weight of the collecting bag 34 itself and any stomal output that accumulates inside the bag is carried by the base wafer's 22 adhesive attachment to the skin surface by the engagement between the first 28 and second 44 halves of the coupling. Thereby, the adhesive material of the adhesive flange 42 in the peristomal skin surface P is not required to have any load bearing capabilities or characteristics and can be optimized towards creating an improved and efficient seal having greater resistance against disintegration or deterioration caused by stomal output attacking the integrity of the adhesive material matrix.

Another advantage, adding to improved anti-leakage characteristics of the ostomy appliance 20 of the disclosure, is that the adhesive material on the adhesive proximal side 24 of the base wafer 22 is less prone to being subjected to aggressive stomal output because the adhesive material of the adhesive flange 42, attached to the collecting bag 34 and providing the seal immediately around the ostomy O, is exchanged with a 'fresh' adhesive flange 42 each time the collecting bag 34 is exchanged (subject to the user's routines or appliance changing pattern). This in effect increases the wear-time of the base wafer 22 and thus in turn reduces the number of times the user has to exchange the base wafer 22. Thus, the user's skin surface is subjected to less taking off and applying of a new weight-carrying portion of adhesive material of an ostomy appliance. This is useful in that fewer changes of adhesive material cause less skin irritation and also provides an economical benefit. Moreover, as an additional advantage, in the context of the present disclosure, the degree of freedom in choosing an applicable kind of coupling mechanism among the many possibilities described above, is greater than usual in that the adhesive material for sealing against the stomal output is exchanged with a new, fresh adhesive wafer 42 each time the collecting bag 34 is exchanged. Relatively flexible, and thus in some cases coupling mechanisms having relatively less coupling strength or force, can therefore be applied because the adhesive on the base wafer 22 does not have to be tailored to withstand stomal output and better maintains its adhesion to the skin surface S. Consequently, a coupling mechanism can be chosen with less regard to load carrying capability of the coupling interface itself because the adhesive on the base wafer 22 maintains its adhesive effect. Moreover, a further advantage is that stomal output is also less likely to reach an interface between the halves of the coupling mechanism itself, which provides inter alia for selection of adhesion-based coupling mechanisms and further helps provide for more comfortable exchanges of the collecting bag (e.g. requiring less cleaning), when no or very little stomal output can reach the coupling interface.

FIG. 2 illustrates some components of embodiments of the ostomy appliance 20 including the base wafer 22 and the collecting bag 34. In embodiments, the base wafer 22 is provided with a first release liner 48 that protects the adhesive proximal side 24 of the base wafer 22 until it is ready to be applied to the skin surface S around the ostomy O of a user. The collecting bag 34 including the adhesive flange 42 is shown to the right of the base wafer 22. Punctured lines indicate how the components of the ostomy appliance 20 are adapted to be connected to each other and to be attached to the skin of the user. In embodiments, the adhesive flange 42 includes a second protective release liner 50 adapted to be removed before applying the adhesive flange 42 to the peristomal skin surface P through the first opening 30 in the base wafer 22. The first half 28 of the coupling attached to the base wafer 22 is configured to connect and couple with the second half 44 of the coupling provided on the proximal wall 36 of the collecting bag 34. In one embodiment, the first half 28 of the coupling is a first annular ring having a first diameter and the second half 44 of the coupling is a second, annular ring having a second diameter that is greater than the first diameter. In one embodiment, the second diameter is smaller than the first diameter. In one embodiment, the first and second annular rings 28, 44 are adapted to be attached to each other in frictional engagement. In embodiments, the collecting bag 34 includes a first comfort layer 37 provided on the external surface of the proximal wall 36 and a second comfort layer 39 provided on the external surface of the distal wall 38. In embodiments, the comfort layers 37, 39 are welded to the walls 36, 38 along peripheral edges where the walls 36, 38 themselves are welded together to define a volume of the collecting bag 34. In embodiments, one or both of the comfort layers 37, 39 include(s) a lateral slit 41 extending from one side of the peripheral edge of the collecting bag 34 to another, thereby defining an opening in the comfort layer(s) 37, 39. In embodiments, the comfort layer(s) 37, 39 is/are attached to the walls 36, 38 in a plurality of locations.

With particular reference to FIGS. 1 and 2, in embodiments, the first opening 30 and the inlet hole 40 are aligned around an axis A-A extending in an axial direction through a first centre C1 of the base wafer 22 and a second centre C2 of the inlet 40.

Figure 3:
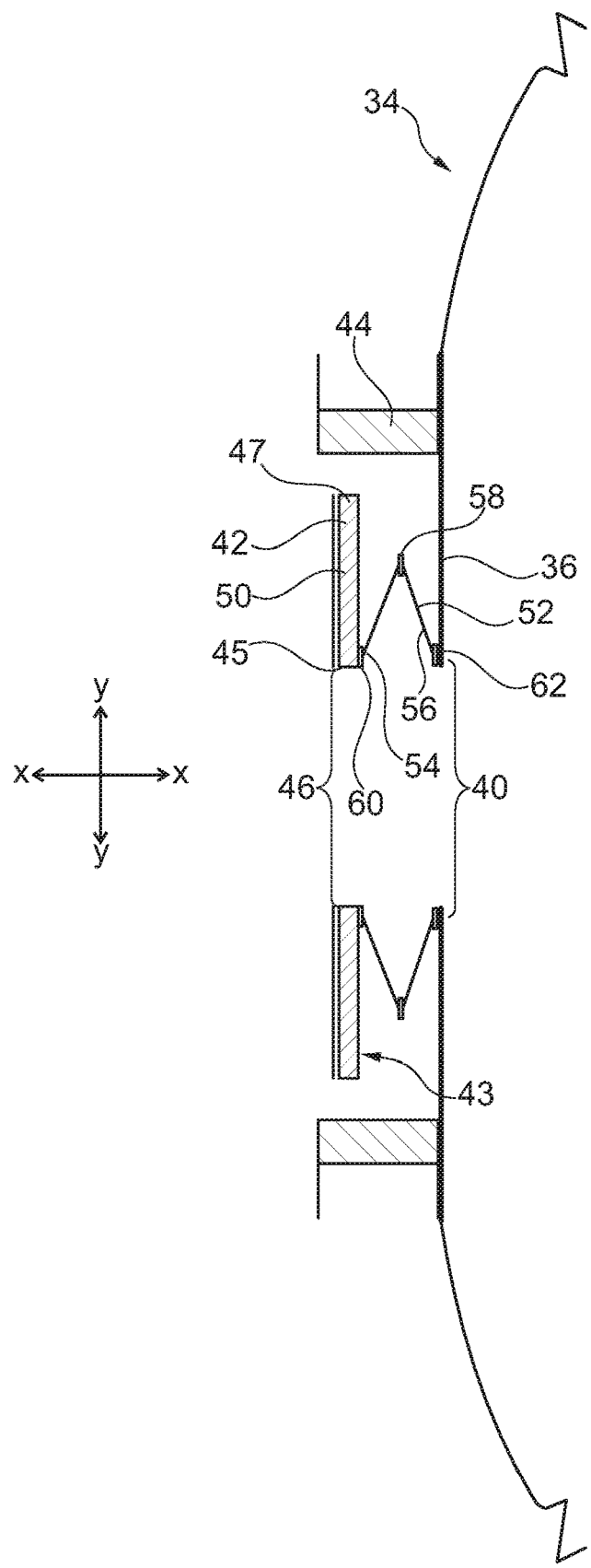
FIG. 3 is a cross-sectional side view of details of one embodiment of an ostomy appliance.

FIG. 3 is a cross-sectional side view of one embodiment of the collecting bag 34 wherein the adhesive flange 42 is floatingly attached to the proximal wall 36 of the bag 34. By 'floatingly' attached is to be understood that the adhesive flange 42 is attached to the collecting bag 34 such that movement of the adhesive flange 42 in a direction Y (up/down in relation to the proximal wall 36) and/or in a direction X (away from/closer to the proximal wall 36), does not necessarily cause an immediate, relative movement of the proximal wall 36 of the collecting bag 34. The 'floating' attachment between the adhesive flange 42 and the proximal wall 36 further helps provide for the effect that the adhesive of the adhesive flange 42 is free from carrying any load of the weight of the collecting bag 34 when it is attached to the skin surface of a user, and also helps to prevent any direct pulling or shear forces, caused by external force applied to the collecting bag 34, from being transferred or translated to the adhesive of the adhesive flange 42.

Figure 4:
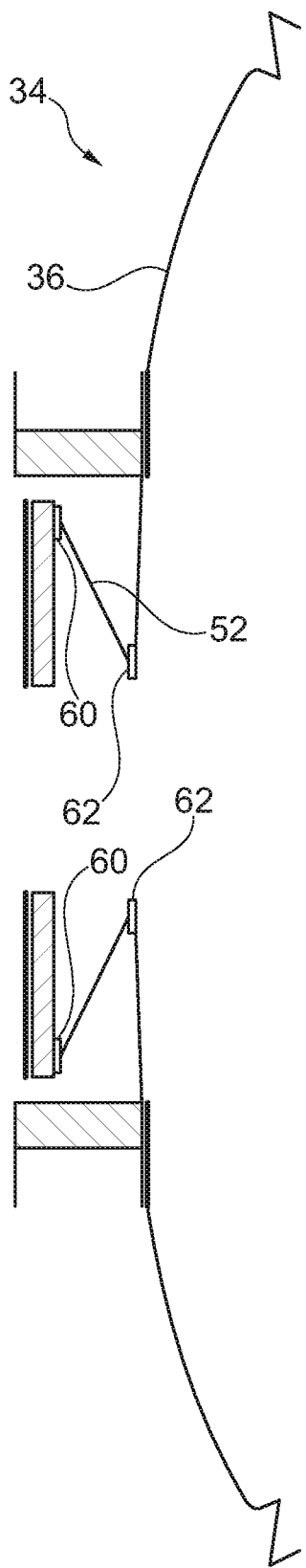
FIG. 4 is a cross-sectional side view of details of one embodiment of an ostomy appliance.

In embodiments, as illustrated by way of examples in FIGS. 3 and 4, the adhesive flange 42 is floatingly attached to the proximal wall 36 with a plastic tube 52. In one embodiment, a first end 54 of the plastic tube 52 is attached to the adhesive flange 42 and a second end 56 is attached to the proximal wall 36 of the collecting bag 34. In one embodiment, the plastic tube 52 includes one or more plications 58 allowing the plastic tube 52 to be extended such that the adhesive flange 42 is movable in relation to the proximal wall 36 of the collecting bag 34. In embodiments, the plastic tube 52 includes a plurality of plications 58 that combine to form an accordion-like structure of the plastic tube 52 between the adhesive flange 42 and the proximal wall 36 of the collecting bag 34. The accordion-like plication(s) 58 of the plastic tube 52 provides for the plastic tube to be extended (stretched) and thereby for the adhesive flange 42 to be movable in the directions of the arrows X and Y.

In one embodiment, illustrated by way of example in FIG. 4, the plastic tube 52 has a straight configuration without any folds, bends or plications. In embodiments, the plastic tube 52 provides a safe and flexible connection between the adhesive flange 42 and the collecting bag 36. In embodiments, the plastic tube 52 is configured with a conical shape such that the plastic tube 52 has a first, relatively smaller diameter at its connection to the proximal wall 36 of the collecting bag 34 and a second, relatively greater diameter at its connection to the adhesive flange 42. In embodiments, the plastic tube 52 is attached to the adhesive flange at a first weld zone 50 and to the proximal wall 36 at a second weld zone 62.

In embodiments, the plastic tube 52 is adapted with an axial extent to allow for an axial displacement of a first plane extending through (containing) the adhesive flange 42 away from a second plane extending through (containing) the proximal wall 36 of the collecting bag 34 along the central axis A-A (FIG. 2).

In embodiments, the plastic tube 52 is adapted with an axial extent to allow for an axial displacement of a first plane extending through the adhesive wafer 42 away from a second plane extending through the proximal wall 36 of the collecting bag 34 along the axis A-A of 10-70 mm. In one embodiment, a first end 54 of the plastic tube 52 is attached to a distal side 43 of the adhesive flange 42 radially closer to a first, inner periphery 45 of the adhesive flange 42 defining the central opening 46 in the adhesive flange 42 than to a second, outer periphery 47 of the adhesive flange 42. One exemplary embodiment including this feature is illustrated in FIG. 3.

In one embodiment, a first end 54 of the plastic tube 52 is attached to the distal side 43 of the adhesive flange 42 radially closer to the second, outer periphery 47 of the adhesive flange 42 than to the first, inner periphery 45 of the adhesive flange 42 defining the central opening 46 in the adhesive flange 42. One exemplary embodiment including this feature is illustrated in FIG. 4. Depending on the location of the attachment of the first end 54 to the distal side 43 of the adhesive flange 42, the degree to which the adhesive flange 42 can be moved in relation to the proximal wall 36 can be differentiated. For example, the embodiment shown in FIG. 3 is configured to provide a higher degree of extendibility/stretchability/movability of the adhesive flange 42 in relation to the proximal wall 36 than the embodiment shown in FIG. 4.

FIG. 4 is a cross-sectional side view illustrating one embodiment of the collecting bag 34 wherein the adhesive flange 42 is floatingly attached to the proximal wall 36 of the collecting bag 34. In the embodiment of FIG. 4, the plastic tube 52 is straight without any plications.

Figure 5:
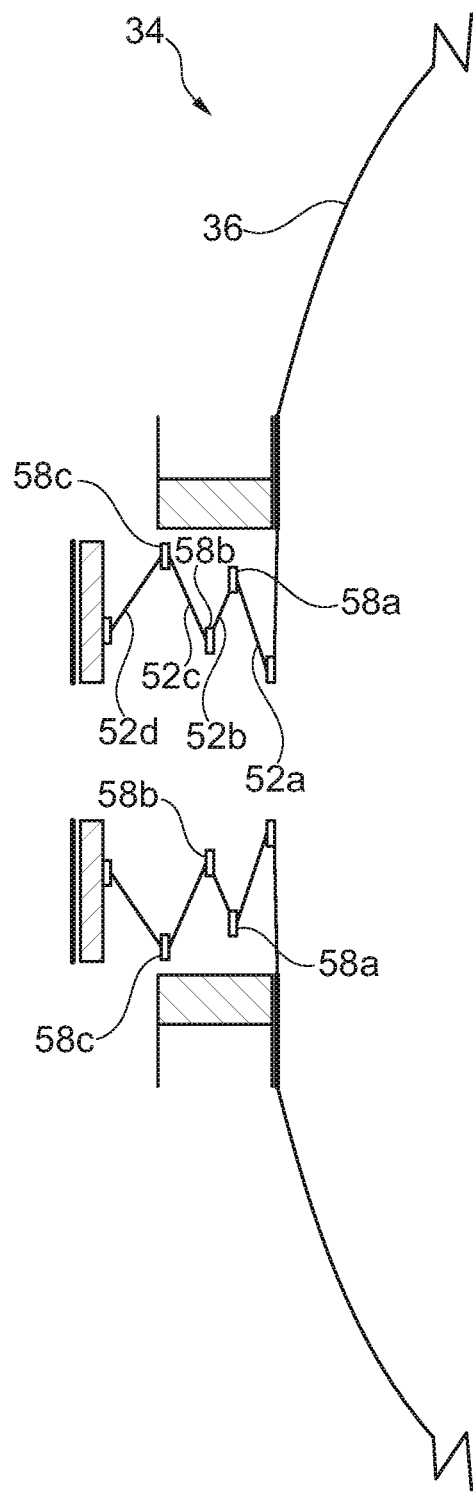
FIG. 5 is a cross-sectional side view of details of one embodiment of an ostomy appliance.

FIG. 5 is a cross-sectional side view illustrating one embodiment of the collecting bag 34, wherein the adhesive flange 42 is floatingly attached to the proximal wall 36 of the collecting bag 34. In the embodiment of FIG. 5, the plastic tube 52 includes a plurality of plications 58a, 58b, 58c. In embodiments, the plications 58a, 58b, 58c are provided by joining together relevant ends of individual plastic layers 52a, 52b, 52c, 52d combining to provide the plastic tube 52 (such as by welding). In turn, the layer 52a is joined to the proximal wall 36 at second weld zone 62, and layer 52d is joined to the adhesive flange 42 at first weld zone 60. In embodiments, the plastic layers 52a, 52b, 52c, 52d are configured (e.g. with different lengths) such that the plications 58a, 58b, 58c are radially displaced or "shifted" in relation to each other and/or to central axis A-A, i.e. the plications do not locate in alignment, or "on top", of each other, if the plastic tube 52 is compressed in its axial direction. Among other advantages, this facilitates the welding processes during manufacture of the ostomy appliance 20.

In one embodiment (with additional reference to FIG. 1), an outer diameter D1 of the adhesive flange 42 is smaller than an inner diameter D2 of the first half 28 of the coupling at a first inner, peripheral edge 32. Thereby, an annular space 29 is provided between the first inner, peripheral edge 32 of the coupling half 28 and a second outer, peripheral edge 31 of the adhesive flange 42. The annular space 29 is useful in helping to provide additional freedom for the adhesive flange 42 to move in relation to the proximal wall 36, particularly in embodiments wherein the adhesive flange 42 is connected to the proximal wall 36 by plastic tube 52.

In one embodiment, an outer diameter D1 of the adhesive flange 42 is sized to adapt the second outer, peripheral edge 31 of the adhesive flange 42 to be placed in frictional contact with the first inner, peripheral edge 32 of the first half 28 of the coupling. Thereby, the adhesive flange 42 and the first half 28 of the coupling can be seen to provide an uninterrupted surface. This helps provide additional security against stomal output engaging with the distal side 26 of the base wafer 22 and/or the distal side 43 of the adhesive flange 42.

In one embodiment, a first adhesive provided on the adhesive proximal side 24 of the wafer 22 has a first initial tack value that is at least three times higher than a second initial tack value of a second adhesive provided on the adhesive flange 42. In other words, the ability of the first adhesive on the wafer 22 to adhere to the skin surface S and create a strong adhesive connection suitable for carrying the weight of the bag 34 and its stomal output contents is advantageously optimized in a direction of providing more (very) secure attachment to the skin surface. In many cases, ostomy appliances currently available on the market are configured with just one single adhesive surface that is required to both create a sufficient sealing against stomal output leakage and be able to adhere well to the skin surface in order to carry the weight of the appliance. This necessarily calls for the provision of an adhesive material with characteristics that is a compromise between fulfilling the required functions of strong enough adhesion and sufficient sealing to provide a satisfactory wear-time of the appliance.

In one embodiment, the second adhesive of the adhesive flange 42 includes a hydrocolloid. In embodiments, the second adhesive of the adhesive flange 42 includes a plurality of different types of hydrocolloids. Using one or more hydrocolloids in the second adhesive material provides an adhesive with optimized moisture absorption capabilities. In one embodiment, the first adhesive of the adhesive proximal side 24 of the base wafer 22 includes one or more hydrocolloids. In embodiments, the amount of hydrocolloids in the first adhesive of the base wafer 22 is less than the amount of hydrocolloids in the second adhesive of the adhesive flange 42 (measured in % w/w before exposure to moisture). In embodiments, the amount of hydrocolloids in the first adhesive includes 1-50% of the amount of hydrocolloids in the second adhesive. In one embodiment, the second adhesive includes an elastic adhesive material. Suitable and non-limiting examples of an elastic adhesive is disclosed in WO 2009/006901. In some embodiments, the elastic adhesive is additionally or alternatively suitable for the first adhesive of the base wafer 22.

Examples of hydrocolloids include polysaccharides, such as starch, glycogen, hemicelluloses, pentosans, gelatin, celluloses, modified celluloses, pectin, chitosan, and chitin. Modified celluloses include methyl cellulose, hydroxypropyl methyl cellulose, carboxymethylcellulose, and hydroxypropyl cellulose. One hydrocolloid is a water soluble or swelling hydrocolloid chosen from the group consisting of polyvinyl alcohols, powdered pectin, gelatin, methyl cellulose, hydroxypropyl methyl cellulose, carboxymethyl cellulose, hydroxypropyl cellulose and mixtures thereof. In one embodiment, the hydrocolloid is carboxymethyl cellulose (CMC).

Figure 6:
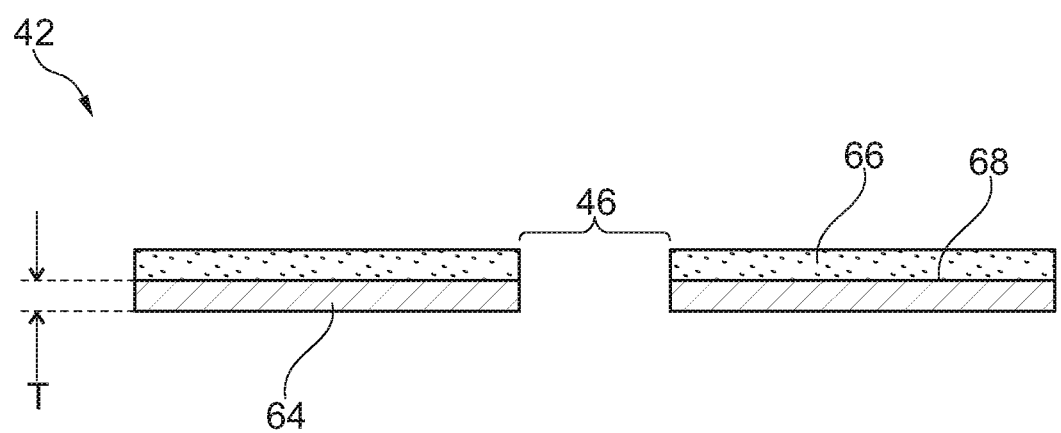
FIG. 6 is a cross-sectional view of an adhesive flange used in embodiments of an ostomy appliance.

FIG. 6 is a cross-sectional view of one embodiment of the adhesive flange 42 including a flexible substrate (or flexible 'backing film') 64 and a central opening 46. In one embodiment, a second adhesive 66 is provided on a proximal surface 68 of the adhesive flange 42. For simplicity, neither the release liner 50 (FIG. 2) nor the proximal wall 36 of the bag 34 (FIG. 2) is shown in the view of FIG. 6. Suitable material examples of the flexible substrate 64 include polymers, such as polyamide (PA), polyethylene (PE) and polyurethane (PU). The flexible substrate of the adhesive flange 42 can be provided with a thickness T in a range from 100-200μ. In one embodiment, the flexible substrate 64 includes a multilayer film material, such as, but not limited to, a PA/PE film, i.e. with one side being made from one of the materials and the other side made from the other material.

In embodiments, a flexible substrate 64 forms a distal-most surface 43 (FIG. 3) of the adhesive flange 42. In embodiments, a first end 54 of a plastic tube 52 is attached to the flexible substrate 64 of the adhesive flange 42 and a second end of the plastic tube 52 is attached to the proximal wall 36 of the collecting bag 34.

In embodiments, a distal-most surface 43 of the adhesive flange 42 is at least partly accessible to one or more fingers of a user at least during application of the adhesive flange 42 to the peristomal skin surface P around the ostomy O of the user. This is advantageous in that it provides an ostomy appliance 20 that is easier for the user to attach to the peristomal skin surface P (the user has access to the at least partly accessible distal-most surface 43 of the adhesive flange 42 during application of the appliance). In embodiments, the second adhesive on the adhesive flange 42 is a pressure sensitive adhesive (PSA) which has better adhesive and sealing characteristics, if the adhesive is manipulated well during application of the ostomy appliance (warming and subjecting to pressure by the user's fingers). By providing easier access to the distal-most surface 43 of the adhesive flange 42, the user has better room for maneuvering and applying pressure with the fingers during application of the appliance. The improved manipulation in turn provides for increased security against disintegration of the adhesive matrix and thus less skin complications and/or loss of adhesion because stomal output is prevented or at least restrained from quickly entering between the adhesive and the skin surface.

In another aspect, the disclosure relates to a collecting bag 36 for a two-piece ostomy appliance having a proximal wall 36 connected to a distal wall 38 along at least a major portion of an outer periphery of a wall 36, 38. An inlet hole 40 is located in the proximal wall 36 of the collecting bag 34, and an adhesive flange 42 is connected to the proximal wall 36 around the inlet hole 40 by a plastic tube 52. A half part 44 of a coupling interface is attached to the proximal wall 36 of the collecting bag 34 at a first radial distance from a centre of the inlet hole 40. The first radial distance is greater than a second radial distance from the centre of the inlet hole 40 to where the plastic tube 52 extending between the adhesive flange 42 and the proximal wall 36 of the collecting bag 34 is attached to the proximal wall 36.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

The invention claimed is:

1. An ostomy appliance comprising:
a base wafer having an adhesive proximal side configured to be attached to a skin surface around an ostomy of a user and a distal side, and a first opening in the base wafer;
a collecting bag for collecting stomal output comprising a proximal wall connected to a distal wall, an inlet hole located in the proximal wall, and an adhesive flange, with a distal surface of the adhesive flange attached directly to the proximal wall around the inlet hole; and
a coupling comprising a first portion attached to the distal side of the wafer and a second portion attached to the proximal wall of the bag;
wherein the second portion of the coupling is separate from the adhesive flange to form a radial space between the adhesive flange and the second portion of the coupling;
wherein, in use of the ostomy appliance, the adhesive flange of the collecting bag is sized for insertion though the first opening in the base wafer for adhesive engagement with a peristomal skin surface around the ostomy of the user, and the radial space is sized to receive the first portion of the coupling for engagement with the second portion of the coupling to attach to the collecting bag to the base wafer.

2. The ostomy appliance of claim 1, wherein the first portion of the coupling includes an annular ring disposed around the first opening, and an outermost diameter of the adhesive flange of the collecting bag is smaller than an inner diameter of the annular ring of the first portion.

3. The ostomy appliance of claim 1, wherein an outer diameter of the adhesive flange is sized to adapt to engage in frictional contact with the first portion of the coupling.

4. The ostomy appliance of claim 1, wherein a first adhesive provided on the adhesive proximal side of the base wafer is configured to have a first initial tack value that is at least three times higher than a second initial tack value of a second adhesive provided on the adhesive flange.

5. The ostomy appliance of claim 1, wherein a second adhesive of the adhesive flange comprises a hydrocolloid.

6. The ostomy appliance of claim 1, wherein a flexible substrate forms the distal-most surface of the adhesive flange.

7. The ostomy appliance of claim 1, wherein the adhesive flange comprises an elastic adhesive.

8. The ostomy appliance of claim 1, wherein the first opening in the base wafer and the inlet hole in the proximal wall of the collecting bag are aligned by engagement of the first portion of the coupling with the second portion of the coupling.

9. The ostomy appliance of claim 1, wherein the first portion of the coupling comprises a first annular ring and the second portion of the coupling comprises a second annular ring adapted for frictional engagement with the first annular ring.

10. The ostomy appliance of claim 1, wherein the first portion of the coupling comprises an annular flange and the second portion of the coupling comprises an annular adhesive ring adapted for adhesive engagement with the annular flange.

11. The ostomy appliance of claim 1, wherein the radial space is formed between the adhesive flange and an inner wall of the second portion of the coupling.

* * * * *

UNITED STATES PATENT AND TRADEMARK OFFICE
CERTIFICATE OF CORRECTION

| | |
|---|---|
| PATENT NO. | : 11,051,971 B2 |
| APPLICATION NO. | : 15/769745 |
| DATED | : July 6, 2021 |
| INVENTOR(S) | : Lars Olav Schertiger |

It is certified that error appears in the above-identified patent and that said Letters Patent is hereby corrected as shown below:

In the Specification

In Column 6, Line 8, delete "collecting bag 36" and insert -- collecting bag 34 --, therefor.

In Column 6, Lines 14-15, delete "first weld zone 50" and insert -- first weld zone 60 --, therefor.

In Column 8, Lines 58-59, delete "collecting bag 36" and insert -- collecting bag 34 --, therefor.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*